United States Patent [19]

Grosselin et al.

[11] Patent Number: 4,925,990

[45] Date of Patent: May 15, 1990

[54] PROCESS FOR THE PREPARATION OF UNSATURATED ALCOHOLS

[75] Inventors: Jean-Michel Grosselin; Claude Mercier, both of Lyons, France

[73] Assignee: Rhone-Poulenc Sante, Antony, France

[21] Appl. No.: 277,150

[22] Filed: Nov. 29, 1988

[30] Foreign Application Priority Data

Dec. 1, 1987 [FR] France .............................. 87 16627

[51] Int. Cl.$^5$ ................. C07C 29/14; C07C 27/04
[52] U.S. Cl. ................... 568/862; 568/813; 568/843; 568/846; 568/861
[58] Field of Search ............... 568/862, 880, 813, 843, 568/861, 862, 846

[56] References Cited

U.S. PATENT DOCUMENTS

| | | | |
|---|---|---|---|
| 3,935,284 | 1/1976 | Kruse | 568/862 |
| 4,024,193 | 5/1977 | Kruse | 568/862 |
| 4,268,454 | 5/1981 | Pez et al. | 568/880 |
| 4,317,946 | 3/1982 | Costa | 568/862 |
| 4,321,414 | 3/1982 | Costa | 568/862 |
| 4,418,227 | 11/1983 | Pez et al. | 568/880 |
| 4,429,056 | 1/1984 | Smith | 568/880 |
| 4,514,521 | 4/1985 | Smith | 568/880 |
| 4,777,302 | 10/1988 | Haji et al. | 568/862 |

FOREIGN PATENT DOCUMENTS

| | | | |
|---|---|---|---|
| 02295890 | 12/1988 | European Pat. Off. | 568/862 |
| 0297752 | 1/1989 | European Pat. Off. | 568/862 |
| 0140030 | 8/1983 | Japan | 568/862 |
| 2024816 | 1/1980 | United Kingdom | 568/862 |

*Primary Examiner*—Werren B. Lone
*Attorney, Agent, or Firm*—Stevens, Davis, Miller & Mosher

[57] ABSTRACT

Unsaturated alcohols are prepared by the hydrogenation of an unsaturated carbonyl compound in a two-phase liquid medium and in the presence of a catalyst consisting of a ruthenium derivative associated with a water-soluble ligand or a complex of ruthenium with a water-soluble ligand.

14 Claims, No Drawings

PROCESS FOR THE PREPARATION OF UNSATURATED ALCOHOLS

The present invention relates to the preparation of primary or secondary unsaturated alcohols by hydrogenation of the corresponding aldehydes or ketones.

More particularly, the present invention provides a process for the preparation of unsaturated alcohols of the formula:

in which each of $R_1$ and $R_2$, which are identical or different, represents a hydrogen atom, a saturated or unsaturated aliphatic radical optionally substituted by a saturated or unsaturated alicyclic radical or by an aromatic radical, a saturated or unsaturated alicyclic radical or an aromatic radical, at least one of $R_1$ and $R_2$ containing an ethylenic double bond, or $R_1$ and $R_2$ together form an unsaturated alicyclic radical, each of the aforesaid aliphatic, alicylic or aromatic radicals being optionally substituted by one or more identical or different alkyl radicals of 1 to 4 carbon atoms, hydroxyl radicals, or alkoxy radicals of 1 to 4 carbon atoms, which comprises hydrogenating a carbonyl compound of the formula:

in which $R_1$ and $R_2$ are as defined above, in a two-phase liquid medium consisting of an organic phase and an immiscible, essentially aqueous phase, with hydrogen in the presence of a catalyst selected from ruthenium derivatives associated with a water-soluble ligand and complexes of ruthenium with a water-soluble ligand.

More particularly, the present invention provides a process for the preparation of $\alpha,\beta$-unsaturated alcohols from the corresponding $\alpha,\beta$-unsaturated carbonyl compounds, i.e. for the preparation of the products of formula (I) in which at least one of the radicals $R_1$ and $R_2$ contains a double bond in the $\alpha,\beta$-position relative to the alcohol group, from the corresponding $\alpha,\beta$-unsaturated compounds of formula (II).

The invention is especially useful for the preparation of $\alpha,\beta$-unsaturated alcohols of formula (I) in which one of the symbols $R_1$ and $R_2$ represents a hydrogen atom and the other represents an aliphatic radical containing 1 to 30 carbon atoms and at least one double bond in the $\alpha,\beta$-position relative to the alcohol group, which is optionally substituted by one or more identical or different radicals selected from alkyl radicals containing 1 to 4 carbon atoms, hydroxyl radicals and alkoxy radicals of which the alkyl part contains 1 to 4 carbon atoms, by an alicyclic radical containing 5 or 6 carbon atoms, which is saturated or unsaturated and optionally substituted by one or more alkyl radicals containing 1 to 4 carbon atoms, or by an optionally substituted phenyl radical, or alternatively $R_1$ and $R_2$ together form an unsaturated alicyclic radical optionally substituted by one or more alkyl radicals containing 1 to 4 carbon atoms, from the corresponding $\alpha,\beta$-unsaturated carbonyl compounds of general formula (II).

More particularly, the present invention provides a process for the preparation of prenol from prenal, nerol/geraniol from citral, crotyl alcohol from crotonaldehyde, and cinnamyl alcohol from cinnamaldehyde.

Carbon-carbon double bonds are easy to hydrogenate using homogeneous catalysis, but carbonyl groups are difficult to reduce by this means especially when they are present in an unsaturated compound and retention of the unsaturation is desired.

It is known to use organometallic complexes based on rhodium [T. Mizoroki et al., Bull. Chem. Soc. Japan, 50, 2148 (1977)] or based on iridium [E. Farnetti et al., J. Chem. Soc. Chem. Comm., p. 746 (1986)] for the selective reduction of cinnamaldehyde to the corresponding unsaturated alcohol. W. Strohmeier and K. Kolke, J. Organometal. Chem., 193, C63 (1980), have described the reduction of crotonaldehyde by means of ruthenium complexes, the best selectivity being obtained with $RuCl_2[P(C_6H_{11})_3]_2(CO)_2$. Finally, K. Hotta, J. Mol. Catal., 29, 105–107 (1985), has shown that citral is converted to geraniol/nerol by hydrogenation in the presence of a complex $RuCl_2[(PPh_3)]_3$, the reaction being carried out in a toluene/ethanol mixture and in the presence of excess hydrochloric acid.

By using the process of the present invention unsaturated carbonyl compounds of formula (II) are selectively converted into unsaturated alcohols of formula (I).

The water-soluble ligands which may be present in the catalysts used in the new process are more particularly the water-soluble phosphines described in French patent 76 22824 (2 366 237), and more especially tri(-metasulphophenyl)phosphine (TPPTS).

The ruthenium derivatives which are particularly suitable for use in the process of the invention are ruthenium halides such as $RuCl_3.xH_2O$, $RuBr_3.xH_2O$ and $RuI_3.xH_2O$, ruthenium oxides such as $RuO_2$, and complex ruthenium salts such as $(NH_4)_3RuCl_6$, $(NH_4)_2RuCl_5(H_2O)$, $K_2RuCl_5(H_2O)$, $Ru(NO)(NO_3)_3$, $Ru(NH_3)_6Cl_3$, $K_2Ru(CN)_6$, $[RuCl(NH_3)_5]Cl_2$ and $K_2[RuCl_5(NO)]$.

The complex of ruthenium with a water-soluble ligand is preferably $RuCl_2(TPPTS)_3$, $H_2Ru(TPPTS)_4$, $HRu(OAc)(TPPTS)_3$, $HRuCl(TPPTS)_3$ or $Ru(CO)_2Cl_2(TPPTS)_2$.

The reaction is generally carried out in water with the product of formula (I) and the starting material of formula (II) forming the organic phase. However, the process can also be carried out in the presence of an organic solvent provided that the reaction mixture forms an organic phase and an immiscible essentially aqueous phase.

Particularly suitable organic solvents are immiscible or only sparingly miscible with water. More particularly, suitable solvents are alcohols (octanol), ethers (ethyl ether, tert-butyl ethyl ether), ketones (methyl isobutyl ketone), aldehydes (benzaldehyde), esters (methyl acetate, ethyl acetate, butyl acetate), and optionally halogenated aliphatic or aromatic hydrocarbons (hexane, toluene, methylene chloride, chloroform, chlorobenzene), and mixtures of such solvents.

The hydrogenation can be carried out at a temperature between −20° and 200° C. and preferably between 0° and 100° C.

The hydrogenation can be carried out under a pressure of 1 to 200 bar and preferably of between 1 and 50 bar.

In general, from 0.001 to 0.01 mol of ruthenium derivative is used per mol of carbonyl compound of general formula (II).

When a ruthenium derivative associated with a water-soluble ligand is used, the amount of ligand used is from 0.1 to 200 mol relative to the ruthenium derivative, and preferably 1 to 100 mol relative to the ruthenium derivative.

It is particularly advantageous to carry out the process according to the invention in a neutral or slightly basic, buffered medium.

Since the catalyst or catalyst system is soluble in water, it can easily be separated with the aqueous phase by decantation, when the reaction is complete, and can thus be recycled.

The process of the invention makes it possible to obtain unsaturated alcohols, and more particularly $\alpha,\beta$-unsaturated alcohols, with a selectivity which is generally greater than 80%.

The alcohols of formula (I) which can be obtained by the process of the invention are intermediates which can be used in organic synthesis. For example, prenol and geraniol/nerol are especially useful in the synthesis of vitamins A and E.

The following Examples illustrate the invention.

EXAMPLE 1

$RuCl_3.3H_2O$ ($10^{-4}$ mol), TPPTS ($4 \times 10^{-4}$ mol), distilled water (7 g), degassed beforehand by bubbling argon for 15 minutes, and prenal ($20 \times 10^{-4}$ mol) are introduced successively into a 25 cc glass flask under an argon atmosphere.

The flask is placed in a 125 cc autoclave. After purging 3 times with hydrogen, a hydrogen pressure of 20 bar is established and the temperature is set at 35° C. The autoclave is shaken.

After 3 hours, analysis of the reaction mixture by gas chromatography shows that:

the degree of conversion of the prenal is 31%, and the distribution of the hydrogenation products is as follows:

| prenol | 25% |
|---|---|
| isoamyl alcohol | 0.5% |
| isovaleraldehyde | 0.2% |
| products not determined | 4% |

The selectivity in respect of prenol is 80%.

EXAMPLE 2

The procedure is the same as in Example 1 except that $RuCl_2(TPPTS)_3$ ($8.5 \times 10^{-5}$ mol), degassed water (6 g) and prenal ($20 \times 10^{-3}$ mol) are used.

After 3 hours of shaking at a temperature of 35° C. and under a hydrogen pressure of 32 bar, analysis of the reaction mixture by gas chromatography shows that:

the degree of conversion of the prenal is 98%, and the distribution of the hydrogenation products is as follows:

| prenol | 82% |
|---|---|
| isoamyl alcohol | 11% |
| products not determined | 5% |

The selectivity in respect of prenol is 83%.

EXAMPLES 3 TO 7

The procedure is the same as in Example 1 except that $RuCl_3.3H_2O$ ($10^{-4}$ mol), TPPTS ($4 \times 10^{-4}$ mol), prenal ($20 \times 10^{-3}$ mol), degassed water (5 cc) and an immiscible solvent (5 cc) are used.

The reaction is carried out under a hydrogen pressure of 20 bar at 35° C.

The results are collated in Table 1.

TABLE 1

| Example | Solvent | Reaction time | Degree of conversion of prenal | Yield of prenol |
|---|---|---|---|---|
| 3 | hexane | 2 h 30 min | 97.5 | 83 |
| 4 | toluene | 1 h 10 min | 96 | 97 |
| 5 | ethyl acetate | 1 h 15 min | 93 | 90 |
| 6 | chloroform | 1 h 10 min | 84 | 96 |
| 7 | methylene chloride | 1 h 30 min | 94 | 88 |

EXAMPLE 8

The procedure is the same as in Example 1 except that $RuCl_3.3H_2O$ ($10^{-4}$ mol), TPPTS ($4 \times 10^{-4}$ mol), a buffer solution of pH 7 (5 cc), toluene (5 cc) and prenal ($20 \times 10^{-3}$ mol) are used.

The reaction is carried out under a hydrogen pressure of 20 bar at 35° C.

After 1 hour 8 minutes, analysis of the reaction mixture by gas chromatography shows that:

the degree of conversion of the prenal is 99%, and the distribution of the hydrogenation products is as follows:

| prenol | 98% |
|---|---|
| isoamyl alcohol | 0.5% |
| isovaleraldehyde | not detectable |

The yield of prenol is 99%.

EXAMPLE 9

The following are introduced successively into a 25 cc glass flask under an argon atmosphere:

$RuCl_3.3H_2O$, 0.032 g ($1.2 \times 10^{-4}$ mol)

TPPTS, 0.32 g ($5.2 \times 10^{-4}$ mol)

Toluene (4.9 g) and water (4.9 g), degassed beforehand by bubbling argon for 15 minutes, are then introduced by means of a transfer tube. Prenal ($21 \times 10^{-3}$ mol) is then added by means of a syringe.

The flask is placed in a 125 cc stainless steel autoclave. After purging 3 times with hydrogen, a hydrogen pressure of 20 bar and a temperature of 35° C. are established. The autoclave is shaken.

After 75 minutes, analysis of the reaction mixture by gas chromatography shows that:

the degree of conversion of the prenal is 98%, and the distribution of the hydrogenation products is as follows:

| prenol | 94% |
|---|---|
| isoamyl alcohol | 1.9% |
| isovaleraldehyde | not detectable |
| t-amyl alcohol | about 2% |

The selectivity is 97%.

After hydrogenation, the flask is taken out of the autoclave and placed under an inert atmosphere. The colourless organic phase is separated off by decantation. The red aqueous phase is washed twice with degassed toluene under an argon atmosphere before being recycled.

The following Table gives the results obtained after each recycling:

| No. of recycling | Hydrogenation time (in minutes) | DC | Y |
|---|---|---|---|
| 1 | 65 | 97 | 95 |
| 2 | 65 | 97 | 92 |
| 3 | 65 | 98 | 92 |
| 4 | 70 | 82 | 97 |

DC: degree of conversion of the prenal
Y: yield of prenol relative to the prenal converted The mean activity of the catalyst is 160 mol of prenal converted per mol of catalyst per hour.

EXAMPLE 10

The following are introduced successively into a glass flask under an argon atmosphere:
RuCl$_3$.3H$_2$O, $1.8 \times 10^{-4}$ mol
TPPTS, $5.5 \times 10^{-4}$ mol
toluene, 4.4 g
buffer mixture of pH 7, 5 g
citral, $9.06 \times 10^{-3}$ mol The flask is introduced into a 125 cc autoclave. After purging 3 times with hydrogen, a hydrogen pressure of 50 bar and a temperature of 50° C. are established. The autoclave is shaken.

After 15 hours, analysis by gas chromatography shows that:
the degree of conversion of the citral is 96.4%, and
the distribution of the hydrogenation products is as follows:

| nerol/geraniol | 94.2% |
|---|---|
| citronellol | 2% |
| citronellal | not detectable |
| tetrahydrogeraniol | not detectable |

The selectivity in respect of nerol/geraniol is 97.7%.

EXAMPLE 11

The procedure is the same as in Example 10 except that the following are used:
RuCl$_3$.3H$_2$O, $10^{-4}$ mol
TPPTS, $4.72 \times 10^{-4}$ mol
hexane, 3.4 g
buffer mixture of pH 7, 5 g
crotonaldehyde, $24 \times 10^{-3}$ mol The reaction is carried out under a hydrogen pressure of 20 bar at 35° C.

After 4 hours, analysis by gas chromatography shows that:
the degree of conversion of the crotonaldehyde is 95.5%, and
the distribution of the hydrogenation products is as follows:

| crotyl alcohol | 92.7% |
|---|---|
| butanal | 1% |
| butanol | 1.7% |

The selectivity in respect of crotyl alcohol is 97%.

EXAMPLE 12

The procedure is the same as in Example 10 except that the following are used:
RuCl$_3$.3H$_2$O, $9.8 \times 10^{-5}$ mol
TPPTS, $4.4 \times 10^{-4}$ mol
toluene, 4.3 g
buffer medium of pH 7, 4.8 g
cinnamaldehyde, $13.2 \times 10^{-3}$ mol The reaction is carried out under a hydrogen pressure of 20 bar at 35° C.

After 3 hours, analysis by gas chromatography shows that:
the degree of conversion is 98.8%, and
the distribution of the hydrogenation products is as follows:

| cinnamyl alcohol | 98.5% |
|---|---|
| 3-phenylpropanal | not detectable |
| 3-phenylpropanol | not detectable |

The selectivity in respect of cinnamyl alcohol is 99.5%.

EXAMPLE 13

Ruthenium chloride (RuCl$_3$) ($5 \times 10^{-4}$ mol) and TPPTS ($17.5 \times 10^{-3}$ mol) are introduced into a 250 cc round-bottomed flask and buffer solution of pH 7 (100 cc) is then added under an inert atmosphere. The dark green solution obtained is transferred by syringe to a 300 cc SOTELEM reactor which has been purged with nitrogen beforehand. After it has been closed, the reactor is purged with nitrogen and then hydrogen, the hydrogen pressure is adjusted to 20 bar and the temperature is adjusted to 50° C. The reactor is stirred at a speed of 1500 rpm for 1 hour. After stirring has stopped and the reactor has cooled to a temperature of about 20° C., it is cautiously degassed and then purged with nitrogen.

Prenal (50 cc) is introduced under a stream of nitrogen. The reactor is purged with nitrogen and then hydrogen. The hydrogen pressure is set at 20 bar and the temperature is set at 50° C. Stirring is adjusted to a speed of 1500 rpm. The hydrogenation takes 30 minutes.

After cooling to a temperature of 20° C., the reactor is cautiously degassed. The reaction mixture is poured into a separating funnel. The aqueous phase is extracted with methylene chloride (3×25 cc).

Analysis of the combined organic phases by gas chromatography shows that:
the degree of conversion of the prenal is 100%, and
the distribution of the hydrogenation products is as follows:

| prenol | 99% |
|---|---|
| isoprenol | 0.6% |
| isoamyl alcohol | 0.2% |
| products not determined | 0.2% |

We claim:
1. A process for the preparation of an unsaturated alcohol of the formula:

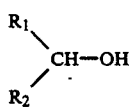

in which each of $R_1$ and $R_2$, which are identical or different, represents a hydrogen atom, a saturated or unsaturated aliphatic radical of 1 to 30 carbon atoms, a saturated or ethylenically unsaturated aliphatic radical of 1 to 30 carbon atoms substituted by a saturated or ethylenically unsaturated alicyclic radical of 5 or 6 carbon atoms or by a phenyl radical, a saturated or ethylenically unsaturated alicyclic radical of 5 or 6 carbon atoms, or a phenyl radical, at least one of $R_1$ and $R_2$ containing an ethylenic double bond, or $R_1$ and $R_2$ together form an ethylenically unsaturated alicyclic radical of 5 or 6 carbon atoms, each of the aforesaid aliphatic, alicyclic or phenyl radicals being unsubstituted or substituted by one or more identical or different alkyl radicals of 1 to 4 carbons atoms each, hydroxyl radicals, or alkoxy radicals of 1 to 4 carbon atoms each, which comprises hydrogenating a carbonyl compound of the formula:

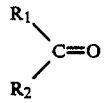

in which $R_1$ and $R_2$ are as defined above, with hydrogen in a two-phase medium consisting of an organic phase comprising the said carbonyl compound and an immiscible, essentially aqueous phase containing a water-soluble catalyst consisting of a ruthenium derivative associated with a water-soluble ligand or a complex of ruthenium with a water-soluble ligand.

2. Process according to claim 1, wherein the catalyst is an inorganic or organic salt oxide, hydride or complex salt of ruthenium associated with a water-soluble ligand.

3. Process according to claim 2, wherein the catalyst is $RuCl_3.xH_2O$, $RuBr_3.xH_2O$, $RuI_3.xH_2O$, $RuO_2$, $(NH_4)_3RuCl_6$, $(NH_4)_2RuCl_5(H_2O)$, $K_2RuCl_5(H_2O)$, $Ru(NO)(NO_3)_3$, $Ru(NH_3)_6Cl_3$, $K_2Ru(CN)_6$, $[RuCl(NH_3)_5]Cl_2$ or $K_2[RuCl_5(NO)]$ associated with a water-soluble ligand.

4. Process according to claim 1, wherein the catalyst is a complex of ruthenium with a water-soluble ligand of formula $RuCl_2L_3$, $H_2RuL_4$, $HRu(OAc)L_3$, $HRuClL_3$ or $Ru(CO)_2Cl_2L_4$, where L represents a water-soluble ligand.

5. Process according to claim 1, wherein the water-soluble ligand is a water-soluble phosphine.

6. Process according to claim 5, wherein the water-soluble phosphine is a sulphonated phenylphosphine.

7. Process according to claim 6, wherein the sulphonated phenylphosphine is tri(metasulphophenyl)phosphine (TPPTS).

8. Process according to claim 1, wherein the organic phase comprises an organic solvent.

9. Process according to claim 8, wherein the organic solvent is an alcohol, ether, aldehyde, ketone, ester, or an optionally halogenated aliphatic or aromatic hydrocarbon, or a mixture thereof.

10. Process according to claim 1, wherein the reaction is carried out at a temperature of between $-20°$ and $200°$ C.

11. Process according to claim 10, wherein the reaction is carried out at a temperature of between $0°$ and $100°$ C.

12. Process according to claim 1, wherein the reaction is carried out under a pressure of between 1 and 200 bar.

13. Process according to claim 12, wherein the reaction is carried out under a pressure of between 1 and 50 bar.

14. Process according to claim 1, wherein the carbonyl compound used as starting material is prenal, citral, crotonaldehyde or cinnamaldehyde and the unsaturated alcohol product is prenol, geraniol/nerol, crotyl alcohol, or cinnamyl alcohol respectively.

* * * * *